(12) United States Patent
Sakai

(10) Patent No.: US 8,114,047 B2
(45) Date of Patent: Feb. 14, 2012

(54) DRUG SOLUTION INFUSION CATHETER

(75) Inventor: Shinichi Sakai, Kanagawa (JP)

(73) Assignee: Piolax Medical Devices, Inc., Yokohama-Shi, Kanagawa-Ken (JP)

( * ) Notice: Subject to any disclaimer, the term of this patent is extended or adjusted under 35 U.S.C. 154(b) by 671 days.

(21) Appl. No.: 11/128,360

(22) Filed: May 13, 2005

(65) Prior Publication Data
US 2005/0256509 A1 Nov. 17, 2005

(30) Foreign Application Priority Data
May 14, 2004 (JP) ................ P2004-144749

(51) Int. Cl. *A61M 37/00* (2006.01)
(52) U.S. Cl. ......................... 604/30; 604/236
(58) Field of Classification Search .................. 604/537, 604/247, 236, 30, 246
See application file for complete search history.

(56) References Cited

U.S. PATENT DOCUMENTS

| | | | |
|---|---|---|---|
| 4,549,879 A | | 10/1985 | Groshong et al. |
| 4,661,094 A | * | 4/1987 | Simpson ............................ 604/8 |
| 4,671,796 A | | 6/1987 | Groshong et al. |
| 4,701,166 A | | 10/1987 | Groshong et al. |
| 5,030,210 A | | 7/1991 | Alchas |
| 5,730,733 A | * | 3/1998 | Mortier et al. ................. 604/527 |

FOREIGN PATENT DOCUMENTS

| | | |
|---|---|---|
| FR | 2 707 505 | 1/1995 |
| FR | 2707505 A1 * | 1/1995 |
| JP | 61-187872 | 8/1986 |
| JP | 2-5975 | 1/1990 |
| JP | 2-5975 (A) | 1/1990 |
| JP | 4-27946 | 3/1992 |
| JP | 5-245210 | 9/1993 |
| JP | 9-501597 | 2/1997 |
| JP | 09501597 W * | 2/1997 |
| NL | 1 000 678 C2 | 12/1996 |
| WO | WO 95/05862 | 3/1995 |
| WO | WO 01/51116 A2 | 7/2001 |

OTHER PUBLICATIONS

Japanese Office Action dated Aug. 19, 2008 with English-Language Translation.

* cited by examiner

*Primary Examiner* — Laura Bouchelle
(74) *Attorney, Agent, or Firm* — McGinn IP Law Group, PLLC

(57) ABSTRACT

A drug solution infusion catheter includes a distal end wall made of an elastic material. The distal end wall closes a distal end surface of the catheter. A center portion of the distal end wall is thinner than a peripheral edge portion of the distal end wall. The center portion of the distal end wall defines a hole or an incision. The hole or the incision closes normally. When a guide wire is pressed against the hole or the incision from an inner side of the catheter or an outer side of the catheter, the hole or the incision elastically opens to allow the guide wire to pass therethrough. An outside of the peripheral edge portion of the distal end wall makes up the distal end surface of the catheter.

22 Claims, 8 Drawing Sheets

DRUG SOLUTION INFUSION CATHETER

BACKGROUND OF THE INVENTION

1. Field of the Invention

The invention relates to a drug solution infusion catheter, which is indwelled continuously or temporarily in a blood vessel such as an artery or a vein, for infusing drug solution such as anticancer drug.

2. Description of the Related Art

Recent years, when administering drug solution such as anticancer drug into a body, infusion of drug solution into a cancer-ridden internal organ is now being performed by inserting a catheter into a blood vessel percutaneously and placing a distal end of the catheter at an entrance of an artery, which continue to the internal organ in question, instead of using an injection syringe or drip infusion.

The catheter is inserted into the blood vessel by a well-known Seldinger technique. In other words, normally, an introduction needle formed of metal is inserted into the blood vessel percutaneously, and then a guide wire is inserted into the blood vessel through the introduction needle to make it reach the intended position. Subsequently, the catheter is inserted along the outer periphery of the guide wire to make it reach the intended position, and then the guide wire is pulled out whereby the indwelling operation of the catheter is completed. By infusing the drug solution into the catheter in this state, the drug solution is infused into the affected area such as an internal organ. However, when a normal catheter is used, there arises a problem that blood may flow backward into the catheter due to the blood pressure.

JP-A-Sho.61-187872 discloses a catheter for administering medicament for a long term. The catheter has a one-way valve at the distal end thereof. The one-way valve is a duckbill valve. The duckbill valve provided at the distal end of the catheter includes a pair of flat bills overlapping with each other. The valve is closed in a normal state. When drug solution is infused, the valve is opened so that the drug solution flows in, whereby backflow of blood is prevented.

JP-U-Hei.4-27946 discloses a catheter with a check valve having a check valve, which allows a guide wire to pass through, at the distal end thereof. The check valve has substantially U-shape in cross section, is mounted so that the distal end is recessed when viewed form the distal end of the catheter, and is formed with a guide wire trough-hole on the bottom (valve base) thereof.

SUMMARY OF THE INVENTION

Since the catheter disclosed in JP-A-Sho.61-187872 is provided with the duckbill one-way valve at the distal end thereof, it is possible to insert the guide wire from the base end side of the catheter, but it is difficult to insert the guide wire from the distal end side of the catheter. When the guide wire is inserted in advance and then the catheter is inserted along the outer periphery of the guide wire, it is necessary to insert the catheter from the rear end of the guide wire. Therefore, the above-described catheter cannot be inserted along the guide wire.

The check valve of the catheter of JP-U-Hei.4-27946 is recessed in a U-shape as described above. Therefore, when the catheter is indwelled in the blood vessel in the body for a long time, the blood tends to be retained in the recessed portion of the check valve. Consequently, the retained blood is coagulated and may result in blood clot.

When infusing drug solution, the catheter is first indwelled in the blood vessel and then, barium meal is infused therein. After having confirmed that the catheter is indwelled precisely at the intended position, drug solution is infused. In that case, if the indwelled position is not correct, the indwelled position is corrected by inserting the guide wire again from the base end side of the catheter, bringing the distal end to the intended position, and moving the catheter along the outer periphery of the guide wire.

However, since the catheter of JP-U-Hei.4-27946 has the check valve being recessed into a U-shape, it is difficult to insert the guide wire from the base end side of the catheter even through it is easy to insert the guide wire from the distal end of the catheter. Hence, there arises a problem in workability in the case of correcting the indwelled position of the catheter.

Accordingly, the invention provides a drug solution infusion catheter in which backflow of blood into the catheter is prevented, drug solution can be infused to an intended position, blood clot due to retention of blood is prevented, and the guide wire can be inserted smoothly either from the distal end side or the base end side, whereby workability and safety during indwelling operation and operation for correcting the indwelled position of the catheter is improved.

In order to achieve the above-described object, according to one embodiment of the invention, a drug solution infusion catheter includes a distal end wall made of an elastic material. The distal end wall closes a distal end surface of the catheter. A center portion of the distal end wall is thinner than a peripheral edge portion of the distal end wall. The distal end wall defines a hole or an incision. The hole or the incision closes normally. When a guide wire is pressed against the hole or the incision from an inner side of the catheter or an outer side of the catheter, the hole or the incision opens to allow the guide wire to pass therethrough. An outside of the peripheral edge portion of the distal end wall makes up the distal end surface of the catheter.

According to this structure, when the drug solution is infused into the catheter, the hole or the incision defined in the distal end wall of the catheter is resiliently opened by the pressure of the drug solution along the direction of infusion of the drug solution, so that the drug solution is infused into an intended site. When the infusion of the drug solution is terminated, the distal end wall is resiliently restored and closed. Hence, backflow of blood into the catheter is prevented, and blood clot due to invasion of blood into the catheter during indwelling of the catheter is also prevented.

The outside of the peripheral edge portion of the distal end wall of the catheter makes up the distal end surface of the catheter. Hence, there is no recess where blood may be retained at the distal end portion of the catheter. Therefore, blood clot due to coagulation of retained blood can be prevented. When the blood clot is formed in the catheter, the blood clot may flow to the end of the blood vessel and causes embolism, whereby the hole or the incision on the distal end wall of the catheter is clogged up, and the infusion of the drug solution may be intercepted.

In addition, the distal end wall of the catheter is formed of elastic material, the center portion thereof is thinner than a peripheral edge portion of the distal end wall, and the center portion of the distal end wall defines a hole or an incision. Therefore, when the guide wire is pressed against the hole or the incision from the inner side of the catheter or the outer side of the catheter, the hole or the incision opens elastically to allow the guide wire to pass therethrough. Accordingly, the guide wire is inserted in the blood vessel in advance until the distal end of the guide wire reaches an intended site to be treated, and thereafter the catheter is inserted from the base end side of the guide wire along the guide wire.

When an operator desires to correct the indwelled position of the guide wire after having inserted the catheter, the correction can be achieved in the following manner. The guide wire is inserted from the rear end side of the catheter, the guide wire is caused to be projected from the distal end portion of the catheter, the distal end thereof is moved to the intended site, and the catheter is inserted along the guide wire. Therefore, workability of the catheter indwelling operation is improved, a burden of the patient is alleviated, and the operation of a medical profession is facilitated.

According to one embodiment of the invention, when viewed from the inner side of the catheter and the outer side of the catheter, the center portion of the distal end wall may be recessed in a taper shape or a spherical shape.

According to this structure, since the center portion of the distal end wall is recessed in a taper shape or a spherical shape, the guide wire is guided to the center portion of the distal end wall by pressing the guide wire from either inside or outside of the distal end wall of the catheter, whereby the hole or the incision defined in the center portion of the distal end wall opens to allow the guide wire to be inserted therethrough easily. Even when blood is flowed in the spherical shape recess on the distal end wall of the catheter, blood is flowed out without staying there for a long time. Hence, formation of blood clot or the like can be prevented.

According to the drug infusion catheter according to the invention, since the guide wire can be inserted from either of distal end side or rear end side of the catheter, the catheter can be inserted along the guide wire, which has been inserted in the blood vessel in advance. Also, when it is desired to correct the position of the distal end portion of the catheter, the position can be corrected by inserting the guide wire from the rear end side of the catheter. Since there is no recess, which may cause retention of blood at the distal end portion of the catheter, blood clot can be prevented.

BRIEF DESCRIPTION OF THE DRAWINGS

FIG. 5 shows an example of insertion of a guide wire from the distal end side of the drug solution infusion catheter, in which

FIG. 7 shows an example of indwelling the drug solution infusion catheter in the body, in which

FIG. 8 shows an example of indwelling the drug solution infusion catheter in the body, in which

DETAILED DESCRIPTION OF THE PREFERRED EMBODIMENTS

Referring now to FIGS. 1 to 9, a drug solution infusion catheter according to an embodiment of the invention will be described.

Figure 1:
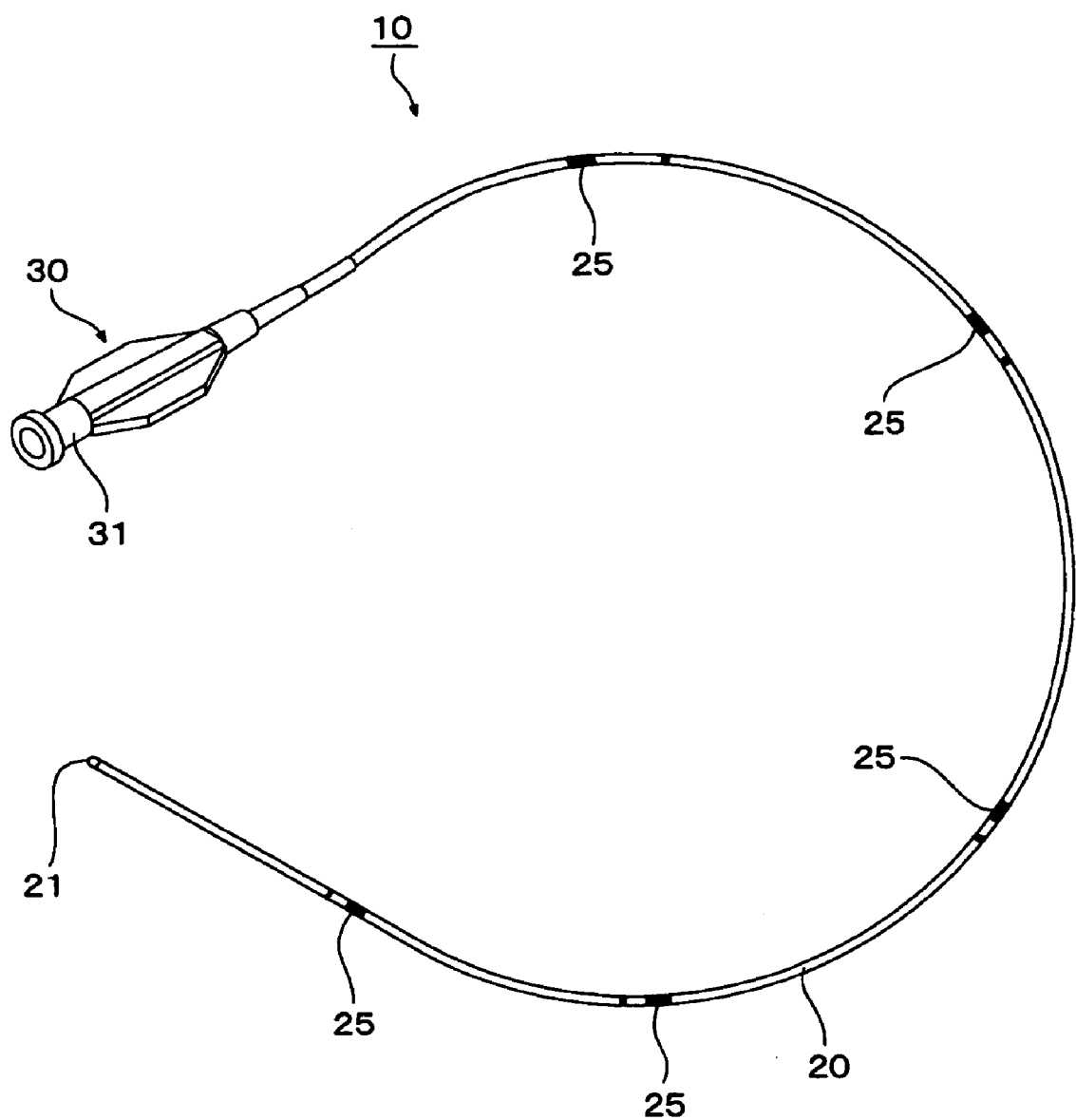
FIG. 1 is a perspective view showing an embodiment of a drug solution infusion catheter according to on embodiment of the invention.

As shown in FIG. 1, a drug solution infusion catheter 10 (hereinafter, referred to simply as catheter 10) includes a catheter main body 20 of a tubular shape, which is made of synthetic resin such as polyurethane, polyamide, polyethylene, polypropylene, silicone, polyvinyl chloride, polyvinyl alcohol, polyvinyl acetate, polystyrene, polyester, polybutadiene; a derivative thereof; a copolymer thereof; a natural high polymer compound such as natural rubber, or a mixture thereof. The catheter main body 20 includes a hub 30 connected to the base end thereof. The hub 30 has a flat shape so as to be easy to grip by hand, and includes an induction pipe 31, which communicates with the catheter main body 20. A guide wire 60 described later is inserted through the induction pipe 31 of the hub 30.

Figure 2A:
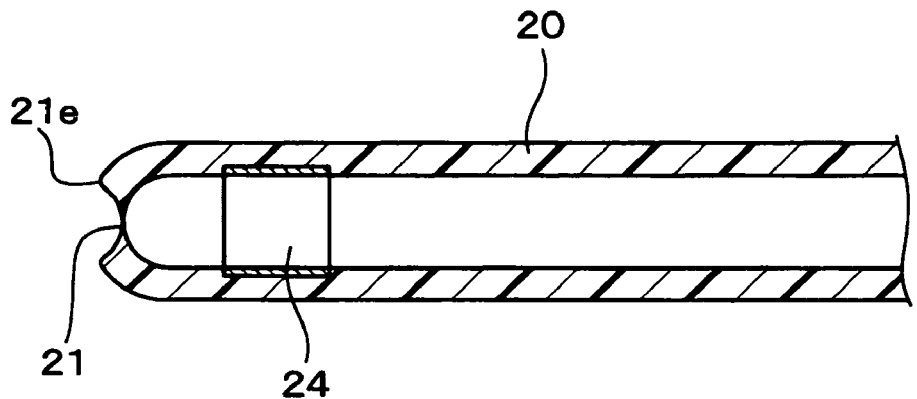
FIG. 2 is a partially enlarged view showing the shape of a distal end wall of the drug solution infusion catheter.
Figure 2B:
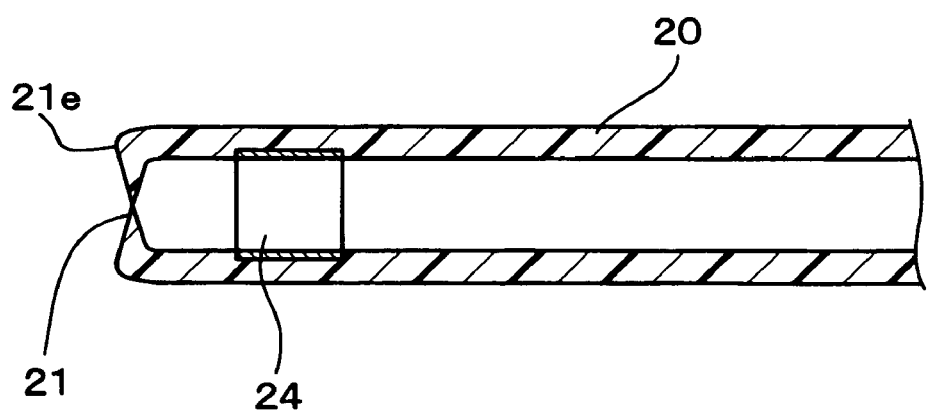

The catheter main body 20 is closed at the distal end by a distal end wall 21. As shown in FIG. 2, the distal end wall 21 is thinned at the center thereof and is thicker at the outer peripheral edge 21*e* thereof. An outer peripheral edge 21*e* forms the distal end of the catheter main body 20. The distal end wall 21 is formed into so-called a bowl shape when viewed either from inside or outside of the catheter main body 20. The shape of the distal end wall 21 may be a spherical shape in which the center thereof is rounded as shown in FIG. 2A, for example, or may be tapered at the center thereof as shown in FIG. 2B, as long as it is thinner at the center and thicker at the outer peripheral edge 21*e* thereof.

Figure 3:
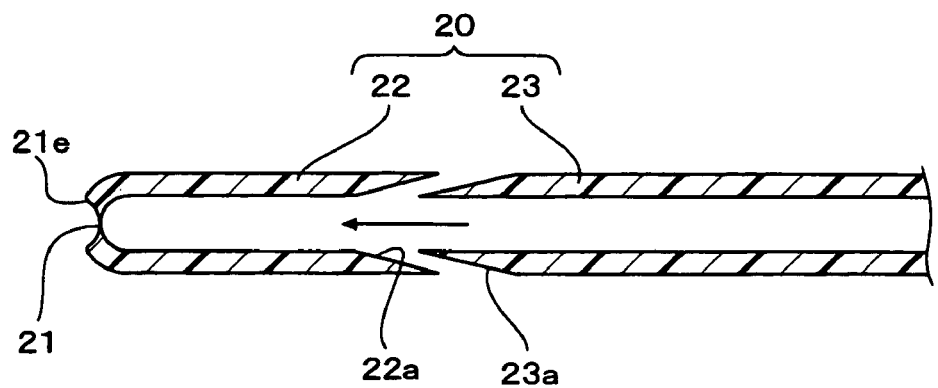
FIG. 3 is a cross-sectional view showing a method of molding a catheter main body of the drug solution infusion catheter.

The distal end wall 21 may be integrally molded with the catheter main body 20 by injection molding or the like. However, if the entire catheter main body 20 including the distal end wall 21 is molded by injection molding, a molding die to be used must be formed in an elongated shape, which is not practical. Therefore, a method including forming a tube 22 provided with the distal end wall 21 as shown in FIG. 3 by cast molding, dipping or injection molding; molding a tube 23, which corresponds to other parts, by extrusion molding; and joining both tubes by adhesion or boding is preferably employed.

An example of joining the both tubes by adhesion will be described. The tube 22 is integrally formed with the distal end wall 21 by injection molding or the like as described above, and includes a tapered surface 22*a* at the end on the opposite side of the distal end wall 21. On the other hand, the tube 23 is molded by extrusion molding or the like, and is formed with a tapered surface 23*a* corresponding to the tapered surface 22*a* of the tube 22 by machining the distal end thereof. Then, the tube 23 is inserted into the tube 22, and arranged so that the tapered surfaces 22*a*, 23*a* abut against each other.

In this state, a mandrel (not shown) formed of metal is inserted from the base end side of the tube 23, and is pushed to a position corresponding to the tapered surfaces 22*a*, 23*a*.

In this state, the portion of the tapered surfaces 22a, 23a abutting against each other is clamped by a metal mold (not shown) including upper and lower molds from the outside thereof. Then, a high-frequency voltage is applied between the metal mold and the mandrel, for effecting dielectric heating, so that the tube 22 and the tube 23 are adhered by heat. This joint method is advantageous in that the high joint strength is achieved since the contact areas of the tapered surfaces 22a, 23a are large.

In addition, hole or incision (in other words, slit or cut) as shown in FIG. 4 is defined in the distal end wall 21 of the catheter main body 20. FIG. 4A shows that hole 21a is defined. In this case, for example, by providing a round projection corresponding to the hole 21a on the metal mold in advance, the hole 21a can be formed simultaneously with the injection molding, whereby manufacturing process may be simplified. The hole 21a is formed into a shape such that while it closes normally, the guide wire 60 can be passed therethrough, and backflow of blood due to a blood pressure at the indwelling site is prevented. The catheter 10 is often indwelled in a vein. Therefore, since the pressure in the vein (venous pressure) is relatively low and the blood is viscous, there is less fear that drug solution flows back due to the blood flow or the blood flows into the catheter, even if the hole 21a as shown in FIG. 4A is provided.

Figure 4A:
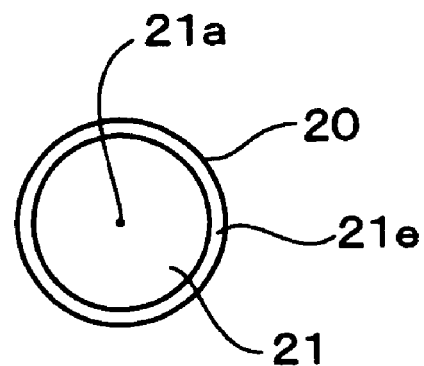
FIG. 4 is an explanatory drawing showing the shape of a hole or incision defined in the distal end wall of the drug solution infusion catheter.
Figure 4B:
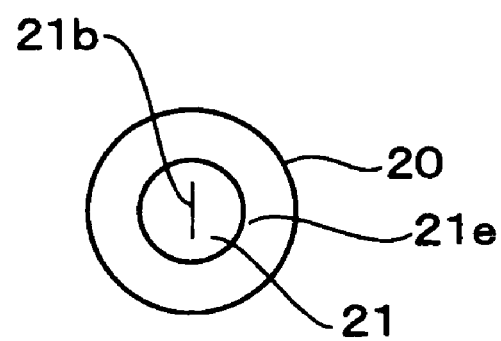
Figure 4C:
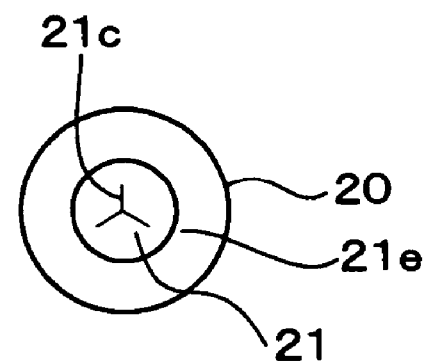
Figure 4D:
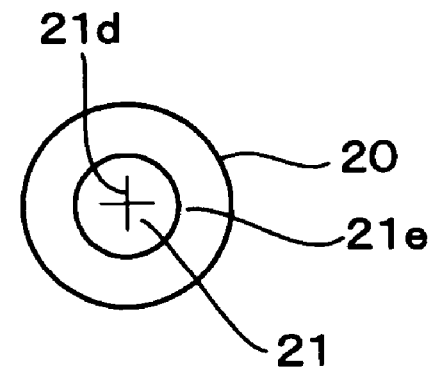

FIG. 4B shows an example in which a linear shaped incision 21b is formed, FIG. 4C shows an example in which a Y-shaped incision 21c is formed, and FIG. 4D shows an example in which a cross-shaped incision 21d is formed. Since all of these incisions 21b, 21c and 21d are relatively simple in shape, it is easy to form those incisions 21b, 21c and 21d. Also, those incisions 21b, 21c, and 21d can open when the drug solution is infused into the catheter main body 20 or when the guide wire 60 is pushed therein. Those incisions 21b, 21c, and 21d can close by the resiliency thereof after having indwelled in the blood vessel.

In this manner, since the hole 21a and the incisions 21b, 21c, 21d are defined in the distal end wall 21, when the drug solution is infused into the catheter 10, the hole 21a or the incision 21b, 21c, or 21d defined in the distal end wall 21 resiliently open by the pressure of the drug solution, so that infusion of the drug solution is achieved. Then, after having completed the infusion of the drug solution, the distal end wall 21 is resiliently restored and closed, so that inflow of blood can be effectively prevented. The incision is preferably of linear-shape, Y-shape, or cross-shape. Forming a larger number of incisions may result in spontaneous opening of the distal end wall 21 due to the blood flow.

The outer peripheral edge 21e of the distal end wall 21 as is makes up the distal end surface of the catheter main body 20, and the distal end wall 21 is not arranged at a deeper position in the catheter 10, a dead void for causing entrance and retention of blood does not exist, whereby blood clot can be prevented.

A marker ring 24 formed of radiopaque material is provided in the vicinity of the distal end of the catheter main body 20, so that the position of the distal end of the catheter 10 when being inserted can be seen by an X-ray monitor or the like. As the marker ring 24, for example, a ring or coil of Au, Pt, Ag, Bi, W or an alloy containing these metals, or of resin mixed with these metals are preferably used.

The inner periphery and/or the outer periphery of the catheter main body 20 is preferably coated, for example, with hydrophilic resin such as polyvinyl pyrrolidone, polyethylene glycol, polyacrylic acid, maleic anhydride copolymer, to improve slippage of the guide wire 60 with respect to the catheter main body 20, to improve slippage of the catheter main body 20 with respect to the inner wall of the blood vessel, and to prevent attachment of blood clot. It is also possible to impregnate or coat the catheter main body 20 with urokinase or heparin for improving anti-blood clot property, or biguanide compound, silver sulfadiazine, or silver protein and so on for providing antifungal properties. Also, a cuff formed of polyester or the like may be mounted to part of the outer periphery of the catheter main body 20 for ensuring fixation with respect to the living body.

There is also a case in which depth marks 25 are formed on the catheter main body 20 at predetermined intervals. The depth marks 25 are for checking how deep the drug solution infusion catheter 10 is inserted into the blood vessel.

Figure 5A:
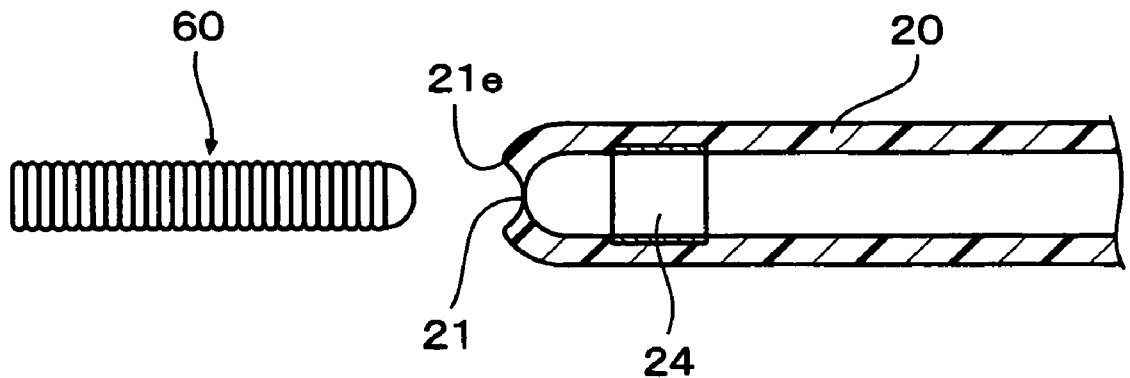
FIG. 5A is a cross-sectional view showing a state before inserting the guide wire.
Figure 5B:
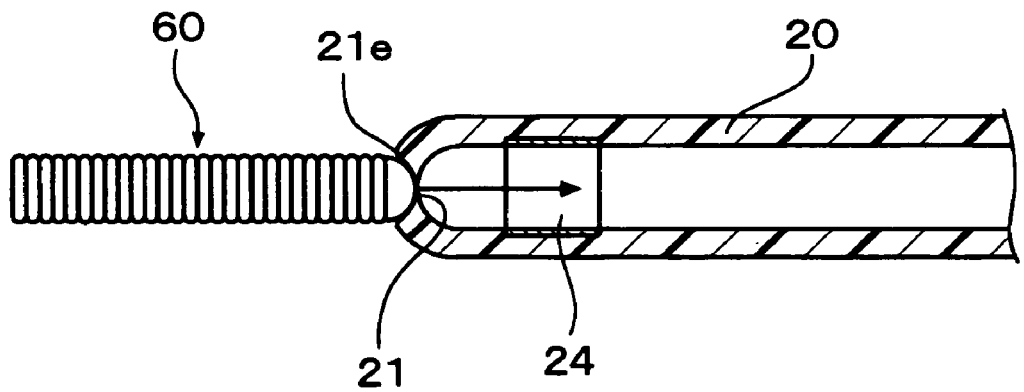
FIG. 5B is a cross-sectional view showing a state in which insertion of the guide wire into the distal end wall is started.
Figure 5C:
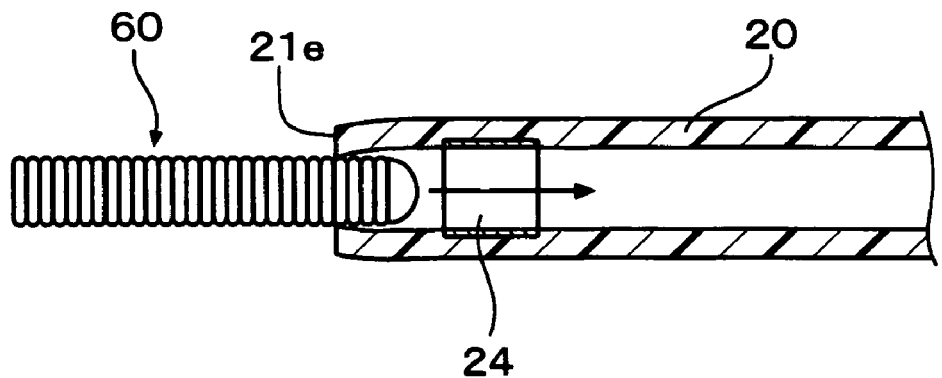
FIG. 5C is a cross-sectional view showing a state in which the guide wire is passed through the distal end wall.
Figure 6:
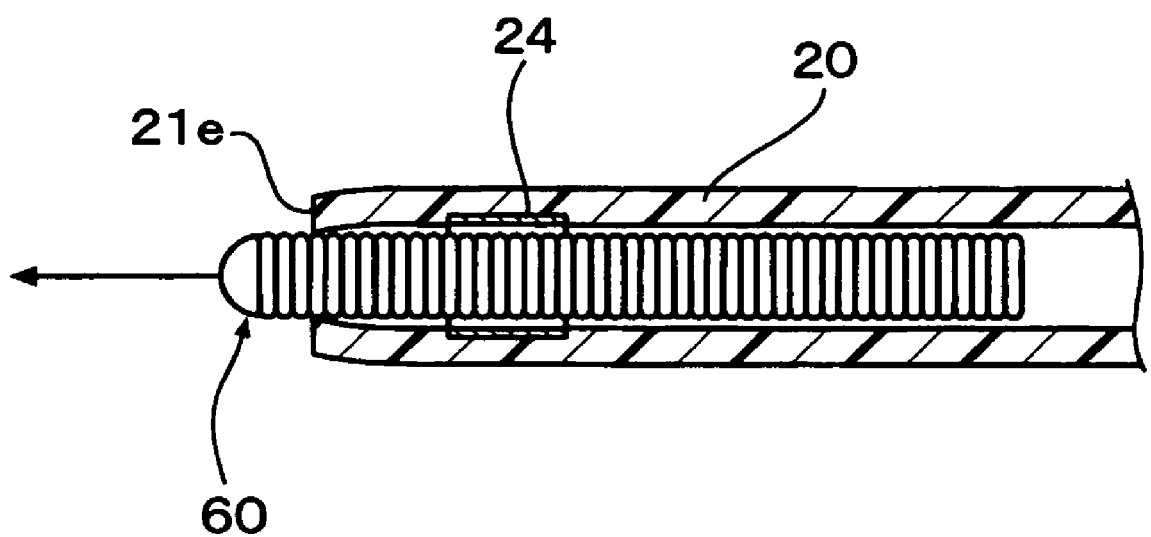
FIG. 6 is a cross-sectional view showing an example in which the guide wire is inserted from the base end side of the drug solution infusion catheter.

FIGS. 5 and 6 show a state when inserting the guide wire 60 into the catheter 10 according to the embodiment. The guide wire 60 of various types, which are publicly known, may be used. In other words, a core wire formed of superelastic alloy or stainless steel, which is coated with synthetic resin film; a core wire with a coil mounted on the outer periphery thereof; and the core wire with the coil further coated with synthetic resin film may be employed.

FIG. 5 shows an example in which the guide wire 60 is inserted from the distal end side of the catheter 10. FIG. 5A shows a state in which the guide wire 60 is disposed on the distal end side of the catheter main body 20. From this state, as shown in FIG. 5B, the guide wire 60 is inserted toward the distal end wall 21 from the distal end side of the catheter main body 20. At this time, even though the position of insertion of the guide wire 60 is slightly misaligned, if the guide wire 60 is simply pushed, the guide wire 60 is spontaneously guided to the center by the bowl-shaped recess on the distal end wall 21. When the guide wire 60 is further pushed in the direction indicated by the arrow, as shown in FIG. 5C, the hole 21a or the incision 21b, 21c or 21d defined in the distal end wall 21 resiliently opens to allow the guide wire 60 to pass therethrough without interfering with moving of the guide wire 60.

FIG. 6 shows a case in which the guide wire 60 is inserted from the base end side of the catheter main body 20 through the hub 30. In this case as well, as in the case shown in FIG. 5C, the hole 21a or the incision 21b, 21c or 21d defined in the distal end wall 21 resiliently opens and allows the guide wire 60 to pass therethrough without interfering with moving of the guide wire 60.

In either cases shown in FIGS. 5 and 6 as described above, when the guide wire 60 is pulled out, the distal end wall 21 is resiliently restored and closed, so that blood is prevented from flowing into the catheter 10.

As shown in FIGS. 5 and 6, the guide wire 60 can be inserted either from the distal end side of the catheter main body 20 or from the base end side of the catheter main body 20 via the hub 30. Accordingly, the indwelling operation of the catheter 10 can be achieved by the steps of, for example, inserting the metallic introduction needle into the blood vessel, then, inserting the guide wire 60, and inserting the catheter 10 along the outer periphery of the guide wire from the distal end side to the intended site. In this case, since the catheter 10 is inserted along the outer periphery of the guide wire 60, the risk of accidentally bursting through the blood vessel wall as in the case of the aforementioned catheter in the related art is reduced and hence the safety level is improved.

On the other hand, correction of indwelled position of the catheter 10 can be performed by inserting the guide wire 60 through the hub 30 from the base end side of the indwelled catheter 10, and then moving the catheter 10 along the outer periphery of the guide wire 60.

In this manner, since the guide wire 60 can be inserted smoothly either from the distal end side or the base end side of the catheter 10, workability and safety for indwelling of the catheter 10 and correction of the indwelled position of the catheter 10 can be improved.

Referring now to FIGS. 7 and 8, a method of administering drug solution such as anticancer drug using the catheter 10 will be described. Reference numeral 71 designates a skin, and reference numeral 72 designates a blood vessel.

Figure 7A:
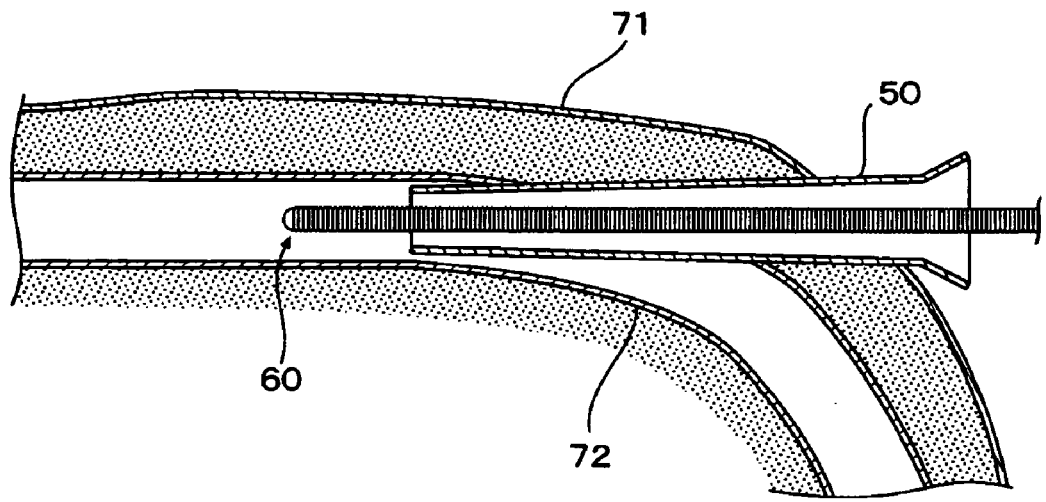
FIG. 7A is a cross-sectional view showing a state in which the guide wire is inserted using a sheath.
Figure 7B:
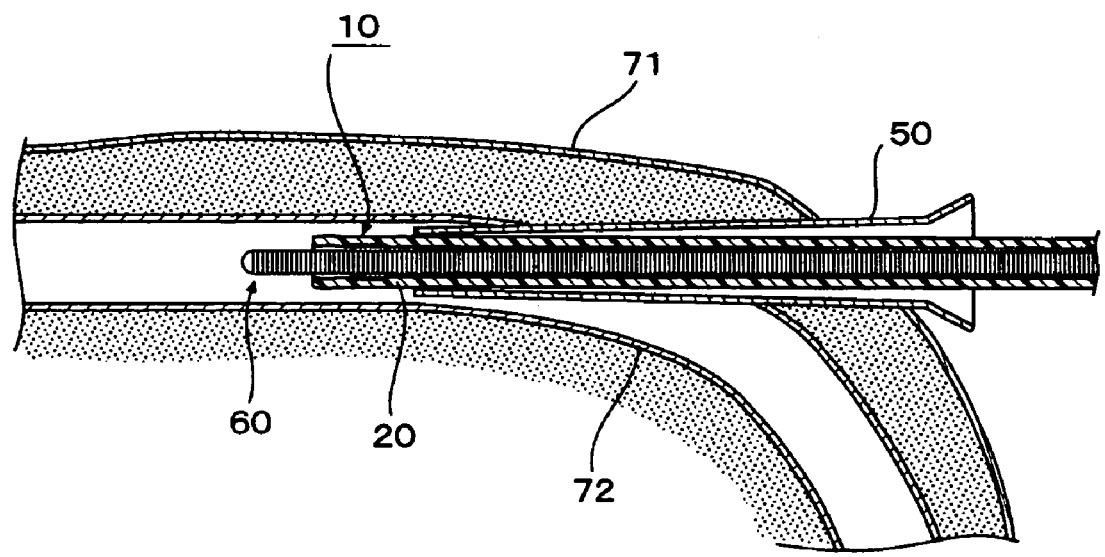
FIG. 7B is an cross-sectional view showing a state in which the catheter is inserted along the outer periphery of the guide wire.

Firstly, as shown in FIG. 7A, a scabbard-shaped sheath 50 is inserted through the skin 71 into the blood vessel 72 by the well-known Seldinger technique. Subsequently, the guide wire 60 is inserted from the base end of the sheath 50, and the distal end of the guide wire 60 is advanced to an intended site in the blood vessel 72, for example, to an entrance of blood into a cancer-ridden internal organ. Then, as shown in FIG. 7(b), the catheter 10 is inserted so as to cover the outer periphery of the guide wire 60 until the distal end of the catheter 10 reaches the distal end of the guide wire 60.

This position can be checked by the marker ring 24 through radioscopy. When the indwelled position is not adequate, the indwelled position of the catheter 10 can be corrected by inserting the guide wire 60 through the hub 30 from the base end side of the catheter 10 again, and then moving the catheter 10 along the outer periphery of the guide wire 60.

In this manner, the distal end of the catheter 10 is disposed at the intended site in the blood vessel 72, for example, to the entrance of blood to the cancer-ridden internal organ.

Figure 8A:
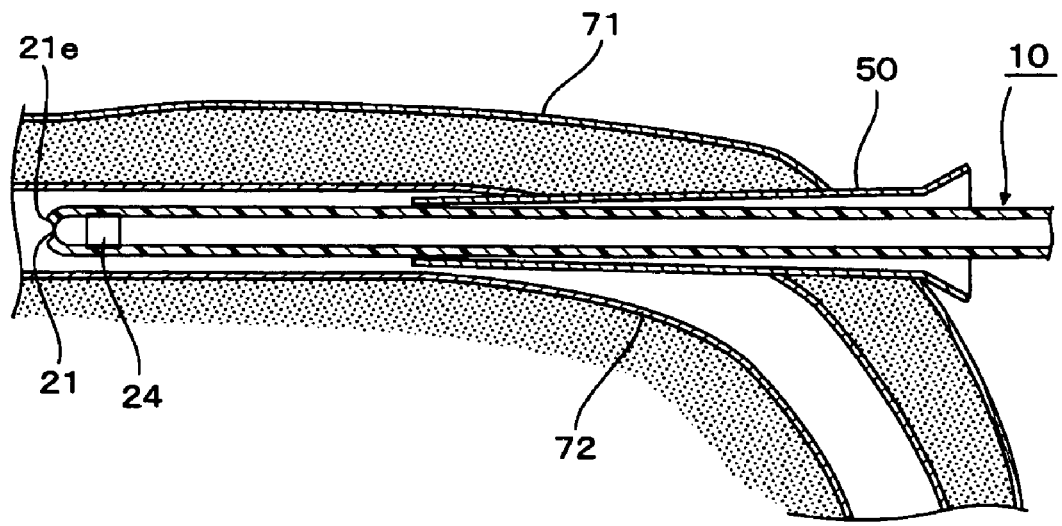
FIG. 8A is a cross-sectional view showing a state in which the guide wire is pulled out and only the catheter is indwelled.

As described above, after having arranged the distal end of the drug solution infusion catheter 10 to the intended site in the blood vessel 72, the guide wire 60 is pulled out completely as shown in FIG. 8A.

Figure 8B:
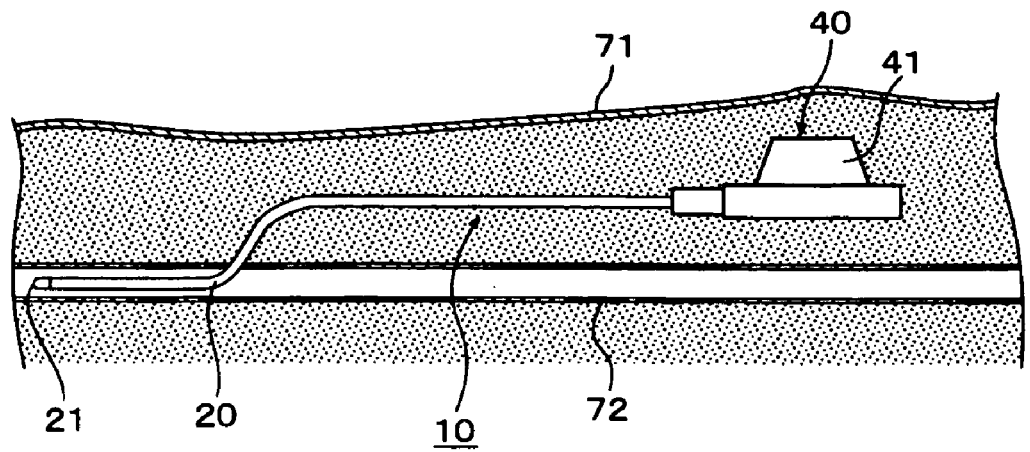
FIG. 8B is an explanatory drawing showing a state in which a drug solution infusion port is connected to the catheter and indwelled in the body.

Then, as shown in FIG. 8B, the sheath 50 is pulled out, the skin 71 is incised, a drug solution infusion port 40 is embedded therein, and the catheter 10 is connected to the drug solution infusion port 40. A portion of the catheter 10 making up a so-called subcutaneous tunnel serves to prevent infection by virus.

Figure 9:
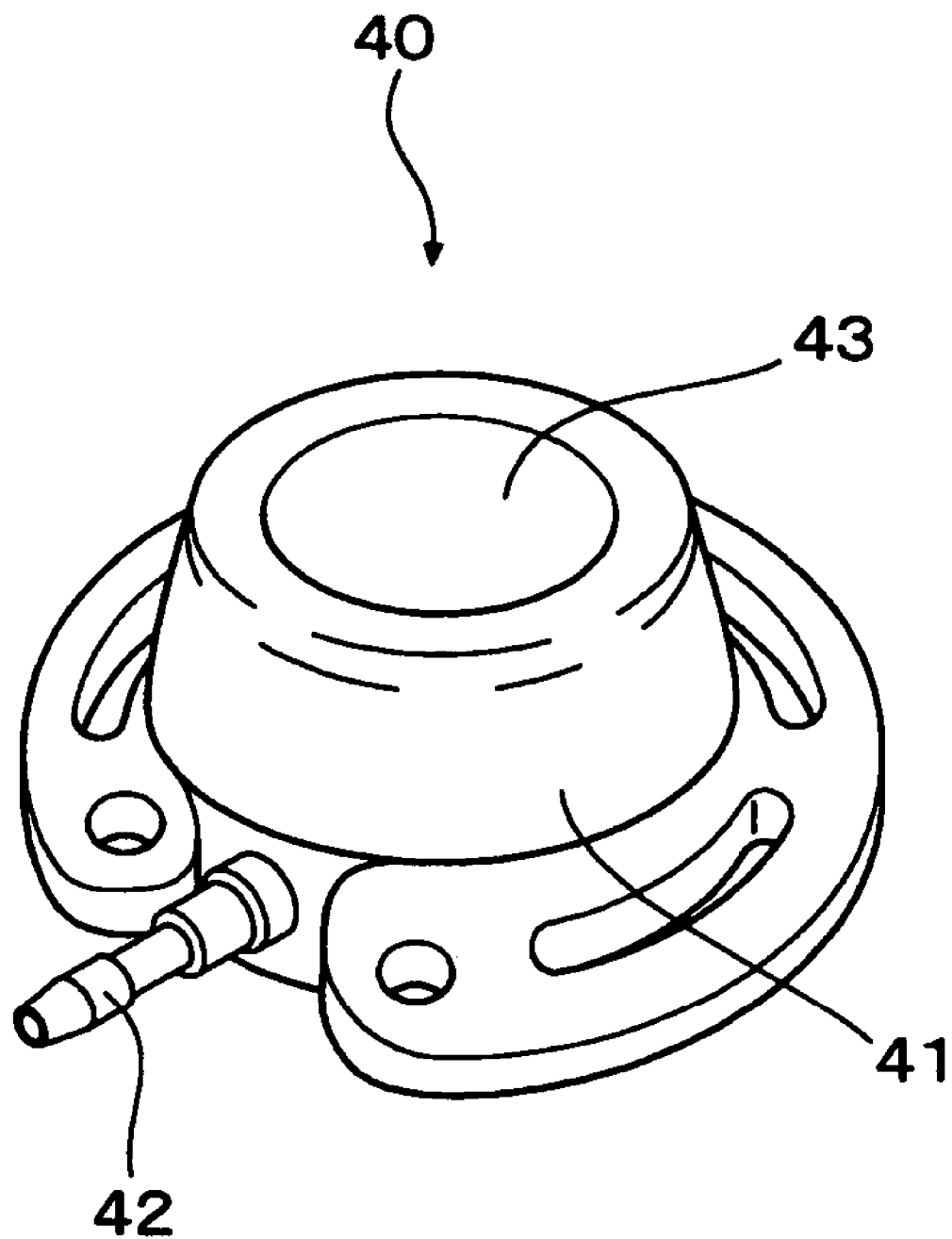
FIG. 9 is a perspective view showing the drug solution infusion port, which is used when the drug solution infusion catheter is indwelled in the body.

As shown in FIG. 9, the drug solution infusion port 40 includes a truncated conical shaped container 41 formed of synthetic resin or metal, which has hardness to a degree that the injection needle or the like cannot pass through; a rubber film 43, which allows the injection needle or the like to be inserted through, mounted at the upper opening of the container 41; and a drug solution discharge port 42 formed on the side wall of the container 41.

Then, when administering the anticancer drug periodically, the injection needle of a syringe (not shown) is punctured into the rubber film 43 at the drug solution port 40 through the skin 71, and the drug solution containing anticancer drug dissolved therein is infused into the drug solution infusion port 40. The drug solution passes through the drug solution infusion catheter 10 from the drug solution discharge port 42 and is discharged from the hole 21a, or the incisions 21b, 21c or 21d defined in the distal end wall 21 of the drug solution infusion catheter 10 so as to be selectively infused to the cancer-ridden internal organ.

The invention is directed to the drug solution infusion catheter, which is indwelled continuously or temporarily in the blood vessel such as the vein, for infusing drug solution such as anticancer drug. The catheter can be used as a drug solution infusion catheter in which backflow of the drug solution is prevented, blood clot due to entrance of blood is prevented, and the guide wire can be inserted either from the distal end side or the base end side of the catheter, whereby workability and safety at the time of insertion of the catheter or correction of the position of insertion can be improved.

What is claimed is:
1. A drug solution infusion catheter comprising:
   a main body formed to allow a guidewire to move therethrough: and
   a distal end wall formed to close a distal end of the main body, the distal end wall comprising an elastic material,
   wherein a center portion of the distal end wall is thinner than a peripheral edge portion of the distal end wall,
   wherein the center portion of the distal end wall comprises a hole or an incision formed to normally close, the hole or the incision being formed at an axis of the main body,
   wherein the distal end wall is formed so as to comprise a resilience such that the center portion remains closed when under a liquid pressure from an outer side of the catheter,
   wherein, when the guide wire is pressed against the hole or the incision from an inner side of the catheter or the outer side of the catheter, the hole or the incision elastically opens to allow the guide wire to pass therethrough, and
   wherein the distal end wall further comprises:
      a first recess that is formed at the inner side of the catheter; and
      a second recess that is formed at the outer side of the catheter.
2. The catheter according to claim 1, wherein when viewed from the inner side of the catheter and the outer side of the catheter, the center portion of the distal end wall is recessed in a taper shape or a spherical shape.
3. The catheter according to claim 1, wherein the distal end wall comprises the incision having a shape selected from a group consisting of a linear shape, a Y- shape, and a cross shape.
4. The catheter according to claim 1, further comprising:
   a marker ring comprising a radiopaque material, wherein:
   the marker ring is disposed in a vicinity of the distal end wall.
5. The catheter according to claim 1, further comprising a main body, wherein:
   at least one of an inner surface and an outer surface of the main body is coated with a hydrophilic resin.
6. The catheter according to claim 1, wherein the hole or the incision resiliently closes after the guide wire passes through.
   wherein the hole or the incision resiliently opens to allow the guide wire to pass through from either the distal end side or from the rear end side, and
   wherein the distal end wall comprises a recess, the recess having a shape that receives the guide wire inserted from either the distal end side or the rear end side, so that the recess guides the guide wire to the center portion of the distal end wall.
7. A drug solution infusion catheter, comprising:
   a main body formed to allow a guidewire to move therethrough;
   a distal end side comprising a distal end wall formed to close a distal end of the main body, the distal end wall comprising an elastic material;
   a rear end side opposite to the distal end side;
   a hole or an incision within a center portion of the distal end wall; and
   wherein a center portion of the distal end wall comprises a hole or an incision formed to normally close, the hole or incision being formed at an axis of the main body,
   wherein the distal end wall is formed so as to comprise a resilience such that the center portion remains closed when under a liquid pressure from an outer side of the catheter, wherein the drug solution infusion catheter is adapted to receive a guide wire from either the distal end side or the rear end side, wherein the hole or the incision resiliently opens to allow the guide wire to pass through from either the distal end side or from the rear end side, and wherein the distal end wall comprises a recess having a shape that receives the guide wire inserted from either the distal end side or the rear end side, so that the recess guides the guide wire to the center portion of the distal end wall.

8. The catheter according to claim 1, wherein a portion of the distal end wall is curved more radially inward toward the axis of the main body than an inner surface of the main body.

9. A method of making a drug solution infusion catheter, comprising:

providing a first tube integrally formed with a distal end wall on a distal end side of the first tube by injection molding, wherein the first tube comprises a tapered surface at an end opposite that of the distal end side;

forming a hole or an incision in a center portion of the distal end wall;

providing a second tube comprising a tapered surface corresponding the tapered surface of the first tube by extrusion molding; and adhering the tapered surfaces of the first tube and the second, tube, wherein the hole or the incision closes normally, wherein the hole or the incision elastically opens to allow a guide wire to pass through, wherein the distal end wall comprises a recess, the recess having a shape that receives the guide wire inserted from either the distal end side or a base end side, so that the recess guides the guide wire to the center portion of the distal end wall, and wherein the distal end wall is formed so as to comprise a resilience such that the center portion remains closed when under a liquid pressure from an outer side of the catheter.

10. The method of claim 9, wherein the tapered surfaces of the first tube and the second tube are adhered by dielectric heating.

11. The method of claim 9, wherein the hole or the incision resiliently closes after the guide wire passes through.

12. The method of claim 9, wherein the distal end wall further comprises a recess on the distal end side of the first tube, the recess adapted to resiliently receive the guide wire from the distal end side of the first tube.

13. The catheter according to claim 7, wherein the catheter further comprises:

a guidewire within the catheter, and a marker ring located on the distal end side of the catheter, wherein the distal end side and the rear end side comprise substantially a same elastic material, and wherein the catheter is coated with a hydrophilic resin comprising at least one of a polyvinyl pyrrolidone, a polyethylene glycol, a polyacrylic acid, and a maleic anhydride copolymer.

14. The catheter according to claim 7, wherein the hole or the incision resiliently closes after the guide wire passes through.

15. The catheter according to claim 7, wherein the hole or the incision resiliently opens by a pressure of a drug solution to allow for an infusion of the drug solution.

16. The catheter according to claim 15, wherein the hole or the incision resiliently closes after the infusion of the drug solution.

17. The catheter according to claim 1, wherein the drug solution infusion catheter is adapted to move along an outer periphery of the guide wire.

18. The catheter according to claim 7, wherein the guide wire is guided to the center portion of the distal end wall by pressing the guide wire from either inside or outside of the distal end wall.

19. The catheter according to claim 7, wherein the hole or the incision elastically opens to allow the guide wire to pass therethrough, if the guide wire is pressed against the hole or the incision from the outer side of the catheter.

20. The catheter according to claim 7, wherein the drug solution catheter further comprises a main body that is integrally molded together with the distal end wall.

21. The catheter according to claim 20, wherein the main body and the distal end wall comprise substantially a same elastic material.

22. The catheter according to claim 1, wherein when viewed from the inner side of the catheter and the outer side of the catheter, the center portion of the distal end wall is recessed in a bowl shape.

* * * * *